US007247140B2

(12) United States Patent
Ophardt

(10) Patent No.: US 7,247,140 B2
(45) Date of Patent: Jul. 24, 2007

(54) DISPENSER WITH SENSOR

(75) Inventor: Heiner Ophardt, Vineland (CA)

(73) Assignee: Gotohti.com Inc., Beamsville, Ontario (CA)

(*) Notice: Subject to any disclaimer, the term of this patent is extended or adjusted under 35 U.S.C. 154(b) by 211 days.

(21) Appl. No.: 11/199,126

(22) Filed: Aug. 9, 2005

(65) Prior Publication Data

US 2006/0041197 A1 Feb. 23, 2006

(30) Foreign Application Priority Data

Aug. 19, 2004 (CA) .................................... 2478578

(51) Int. Cl.
*A61B 8/00* (2006.01)

(52) U.S. Cl. ....................................... 600/437; 250/372

(58) Field of Classification Search ................ 250/372; 600/437

See application file for complete search history.

(56) References Cited

U.S. PATENT DOCUMENTS

| | | | |
|---|---|---|---|
| 3,576,277 | A | 4/1971 | Blackmon |
| 4,722,372 | A | 2/1988 | Hoffman |
| 4,946,070 | A | 8/1990 | Albert |
| 5,186,360 | A | 2/1993 | Mease |
| 5,458,147 | A | 10/1995 | Mauerhofer |
| 5,477,984 | A | 12/1995 | Sayama |
| 5,549,273 | A | 8/1996 | Aharon |
| 5,695,091 | A | 12/1997 | Winings |
| 5,836,482 | A | 11/1998 | Ophardt |
| 5,855,356 | A | 1/1999 | Fait |
| 5,868,311 | A | 2/1999 | Cretu-Petra |
| 5,930,146 | A | 7/1999 | Takenaka |
| 6,161,726 | A | 12/2000 | Parsons |
| 6,206,340 | B1 | 3/2001 | Paese |
| 6,209,751 | B1 | 4/2001 | Goodin |
| 6,209,752 | B1 | 4/2001 | Mitchell |
| 6,279,777 | B1 | 8/2001 | Goodin |
| 6,293,428 | B1 | 9/2001 | Chen |
| 6,386,390 | B1 | 5/2002 | Tinker |
| 6,388,609 | B2 | 5/2002 | Paese |
| 6,390,329 | B1 | 5/2002 | Maddox |
| 6,393,634 | B1 | 5/2002 | Kodaira |
| 6,404,837 | B1 | 6/2002 | Thompson |
| 6,577,240 | B2 | 6/2003 | Armstrong |
| 6,707,873 | B2 | 3/2004 | Thompson |
| 2002/0134800 | A1 | 9/2002 | Johnson |

*Primary Examiner*—Philippe Derakshani
(74) *Attorney, Agent, or Firm*—Riches, McKenzie & Herbert LLP

(57) ABSTRACT

A product dispenser incorporating radiation sensor preferably for ultra violet radiation and preferably with an alarm or notification mechanism which provides indications of ultra violet radiation levels and which may activate the alarm and notification mechanism and/or the product dispenser having regard to ultra violet radiation levels sensed.

19 Claims, 4 Drawing Sheets

DISPENSER WITH SENSOR

SCOPE OF THE INVENTION

This invention relates to product dispensers and more particularly to product dispensers incorporating radiation sensors, preferably an ultra violet radiation sensor.

BACKGROUND OF THE INVENTION

Exposure of humans to sunlight which includes ultra violet radiation is reported to be a principle cause of harmful sunburn and skin cancer. The present invention appreciates known product dispensers suffer the disadvantage that they do not provide any indication to persons as to the level of ultra violet radiation.

SUMMARY OF THE INVENTION

To at least partially overcome these disadvantages of previously known devices, the present invention provides a product dispenser incorporating radiation sensor preferably for ultra violet radiation and preferably with an alarm or notification mechanism which provides indications of ultra violet radiation levels and which may activate the alarm or notification mechanism and/or the product dispenser having regard to ultra violet radiation levels sensed.

In one aspect the present invention provides in combination: (i) a radiation sensing mechanism, (ii) an alarm mechanism, and (iii) a dispensing mechanism, the radiation sensing mechanism sensing electromagnetic radiation preferably ultra violet radiation and providing output signals when the radiation is above predetermined levels, the alarm mechanism when activated by the output signals providing an audible or visual alarm perceptive to a person in proximity of the dispensing mechanism, the dispensing mechanism adapted to dispense product on demand by a user.

BRIEF DESCRIPTION OF THE DRAWINGS

Further aspects and advantageous of the present invention will be apparent from the following description taken together with the accompanying drawings which.

DETAILED DESCRIPTION OF THE DRAWINGS

Figure 1:
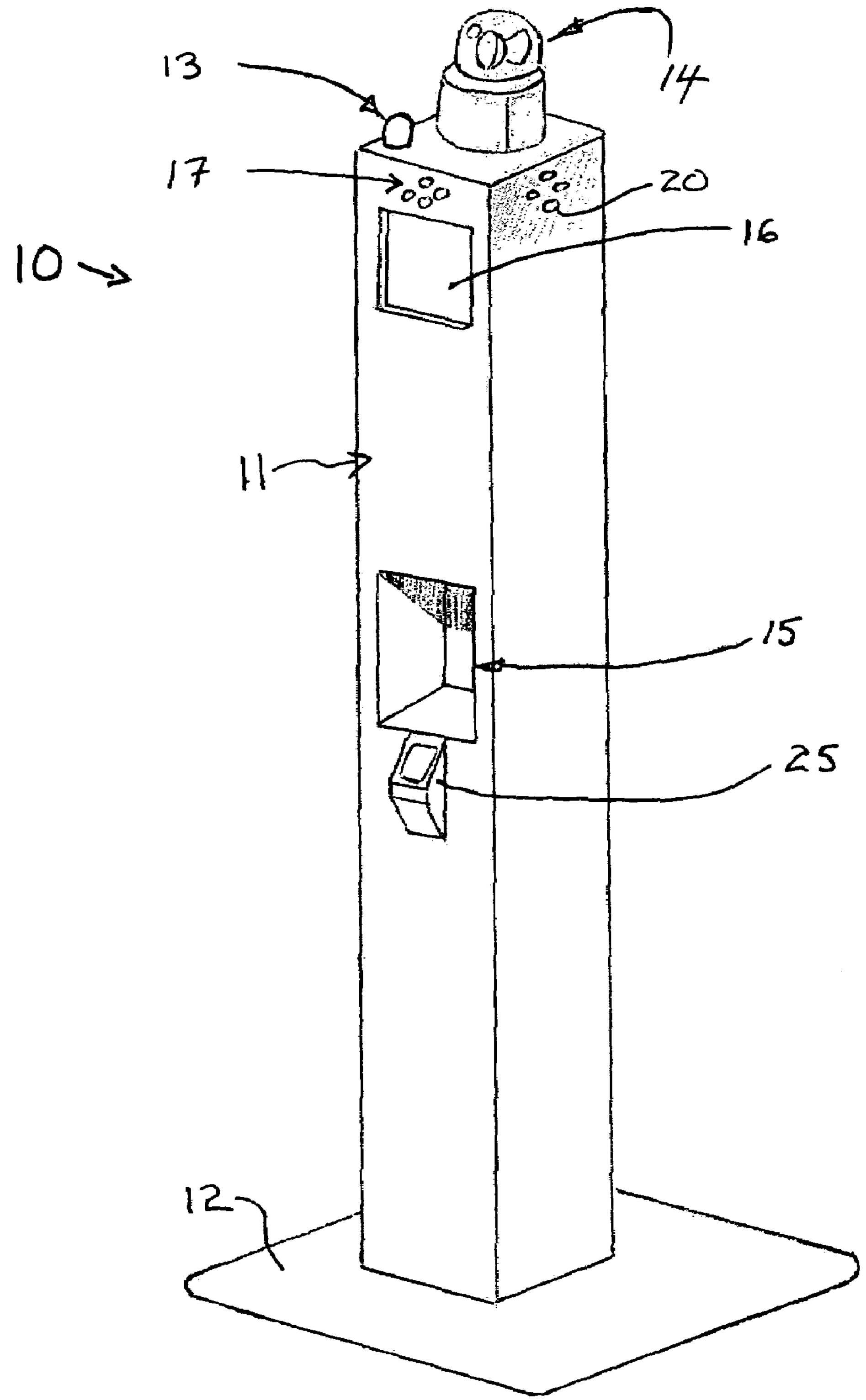
FIG. 1 is a pictorial view of a dispenser in accordance with a first embodiment of the present invention.

Referring to FIG. 1, a dispenser 10 is illustrated having a vertically extending tower 11 supported on a ground-engaging base 12 such that the dispenser may be placed at any location supported by its base 12.

Tower 11 carries a radiation sensor 13, a warning light 14, and a fluid dispensing mechanism 15, a visual display panel 16 and an audible signaling device 17.

Figure 2:
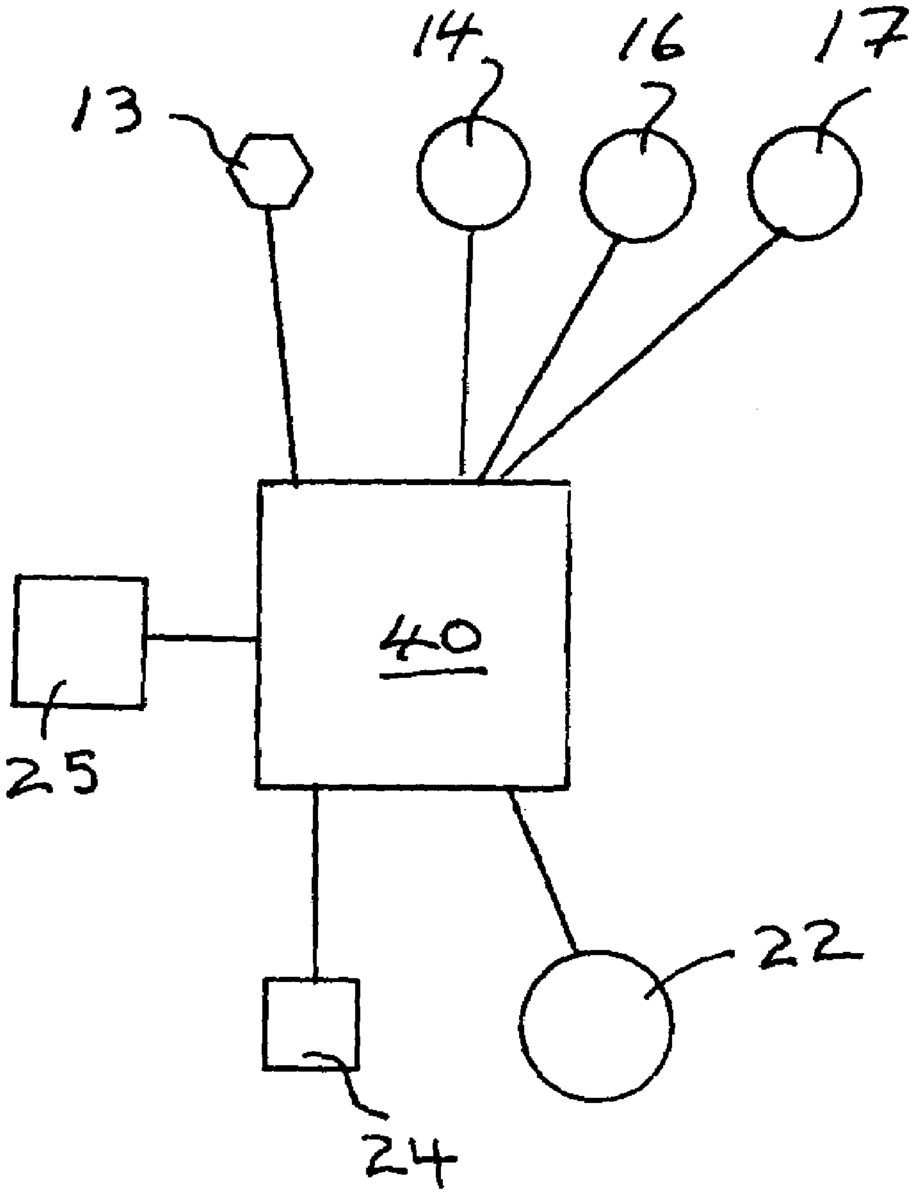
FIG. 2 is a schematic control diagram for the dispenser of FIG. 1.

The sensor 13 preferably senses the level of ultra violet radiation impinging on the tower at any time. A control mechanism 40 shown schematically in FIG. 2, preferably monitors the level of ultra violet radiation sensed by the sensor 13 and provides output signals dependent on the level of the ultra violet radiation sensed. When the ultra violet radiation sensed is above a predetermined maximum level, the warning light 14 is activated so as to visually warn persons in the proximity of the dispenser 10 of the ultra violet radiation level.

The tower 11 also includes a visual display 16 preferably comprising a computer controlled screen upon which text messages may be displayed or at least on which selected predetermined text messages may be illuminated to render them visible. The display panel 16 may be controlled by a control mechanism so as to display suitable notifications, alarms and the like dependent upon the level of the ultra violet radiation sensed by the sensor 13. For example when the ultra violet radiation level is below predetermined levels, the display may suitably provide an indication of safe levels.

Figure 3:
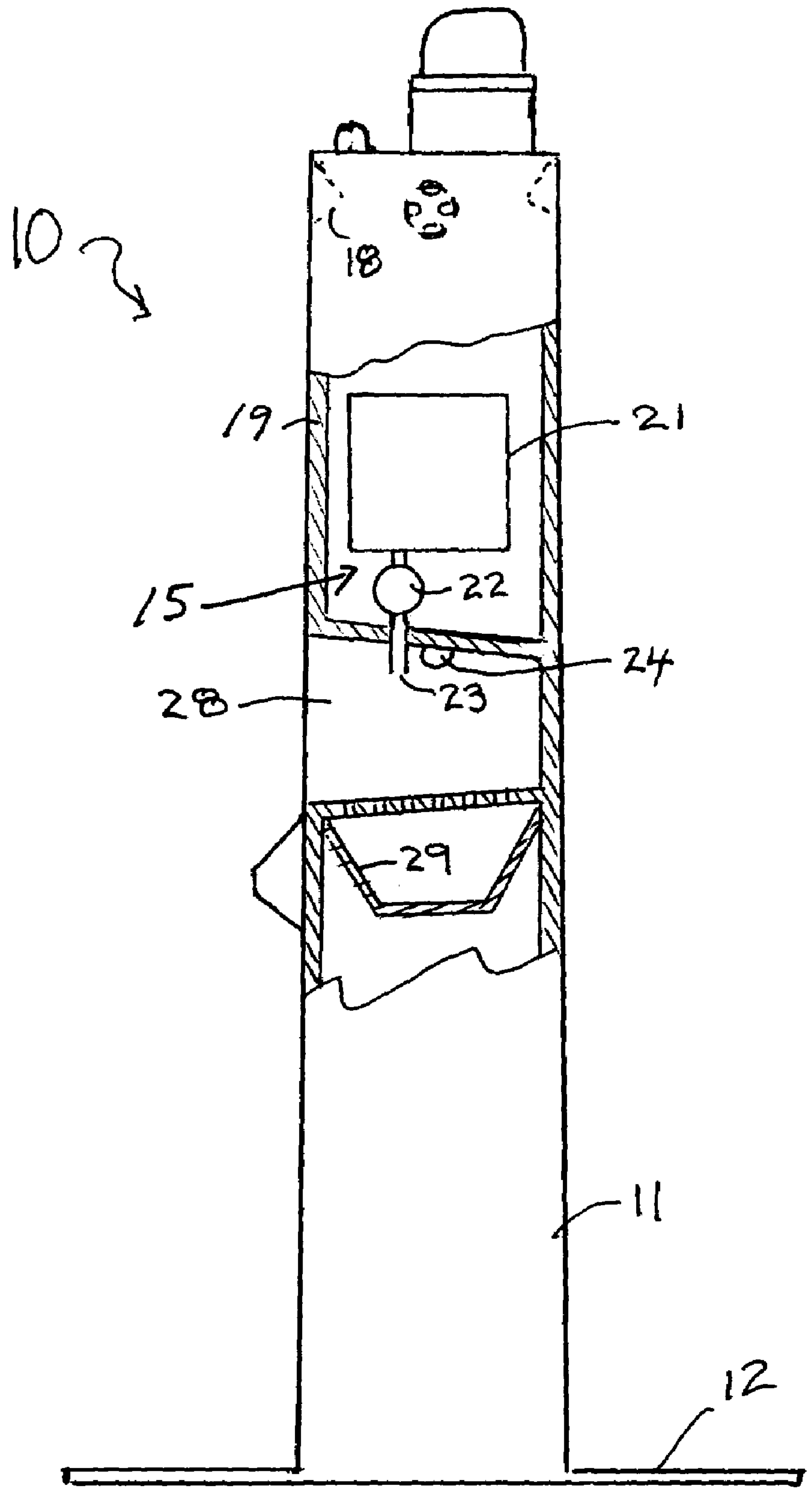
FIG. 3 is a schematic cross-sectional side view of the dispenser of FIG. 1.

The display tower 11 also includes an audible signaling device 17 preferably comprising as seen in FIG. 3 a loud speaker 18 shown in dashed lines disposed in the tower behind a housing wall 19 a plurality of sound transmitting openings 20. One or more loud speakers are preferably provided on each of the four sides of the tower 11 to assist in providing audible signals not only forwardly towards a user of the dispensing mechanism but also 360 degrees about the tower 11.

Various audible signals and warning such as spoken messages, beeps, sounds or other notifications or alarms may be provided by the loud speakers as controlled by the control mechanism based on the level of radiation being sensed.

The dispenser 10 includes as dispensing mechanism 15 a touchless fluid dispenser of the type disclosed in the applicant's U.S. Pat. No. 5,836,482 to Ophardt issued Nov. 17, 1998, the disclosure of which is incorporated herein by reference. The dispenser mechanism 15 is schematically shown in FIG. 3 as including a liquid reservoir 21 for material to be dispensed, a pump 22 which can be activated to dispenser liquid from an outlet indicated as 23 and a sensor indicated as 24 to sense the presence of a user's hand underneath the outlet 23.

The control mechanism preferably controls dispensing of fluid in a desired manner.

One preferred manner of operation is to control the dispensing mechanism 15 so as to be in an inactive mode in which it will not dispense fluid even if requested by a person when the ultra violet radiation sensed is below a predetermined level. When the ultra violet radiation is sensed to be above a predetermined level then the dispensing mechanism is controlled to be in an active mode in which when requested it will dispense fluid. This is advantageous such that at times as when radiation levels are low and it is not desired that fluid be dispensed that fluid cannot be dispensed.

The dispenser 10 illustrated in FIG. 1 is provided with an optional fingerprint reader 25. The fingerprint reader 25 provides a means of identifying an individual user. In one preferred manner of operation, when the pump dispensing mechanism is in an active mode, as a prerequisite to dispensing an allotment of material, a user must have their fingerprint read. The fingerprint reader 25 and the control mechanism 40 can be used to prevent the dispensing of additional amounts of fluid to the same person after dispensing of an initial allotment, at least until some period of time may have passed. The fingerprint reader 25 is not necessary but preferred. The fingerprint reader 25 can also be used to limit activation of the dispensing mechanism for dispensing merely to persons whose fingerprints are of record in a database stored in memory by the control mechanism 40.

The dispensing mechanism 15 is shown with the fluid outlet 23 provided in an internal recess 28 within the tower 11 and with an overflow catch basin 29 below the outlet 23 to catch and engage any overflow of dispensed fluid.

The preferred materials to be dispensed by the dispenser 10 are not limited, and include for example skin creams, lotions or pastes which can assist in protection, guarding and nurturing the human skin against the effects of sunlight. The fluids to be dispensed may comprise impermeable sun blocks, tanning oils, sunscreens and absorbers of ultra violet radiation although the particular nature of the material or fluid to be dispensed is not limited. Preferred fluids to be dispensed are commonly known as sunscreens which include components which assist in reducing the effect of sun radiation notably ultra violet radiation on human skin.

The warning light 14 preferably provides a plurality of flashing amber and/or red coloured lights which may rotate or flash alternatively. The light 14 may comprise a combination of different coloured lights such as green, yellow or amber and red with different of these lights to controlled by the control mechanism 40 be flashed or turned on having regard to different conditions sensed by the radiation sensor 13.

The radiation sensor 13 preferably provides output signals to be received by the control mechanism 40. The control mechanism 40 controls operation of the various warning/notification mechanisms including the warning light 14, the visual display panel 16 and the audible signal device 17. The control mechanism 40 also preferably controls the operation of the dispensing mechanism 15. Various factors may be used as inputs to assist in control of operation of the dispenser 10 including amongst others the time of day, the latitude, longitude and altitude where the tower 11 is located, levels of radiation measured at any time or cumulatively over time, changes of radiation levels with time, temperature as may be sensed by a thermometer (not shown) and humidity which may be sensed by a humidity sensor (not shown).

Factors such as the time, latitude, longitude, altitude and relative location of the tower 11 can be used for example to prevent the dispenser being activated at a time when the tower is in darkness or possibly towards the end of a day when the radiation levels are naturally to be decreased. The radiation levels at any time can be considered by the control mechanism having regard to time and location to determine expected increases in radiation with time.

Measuring radiation levels over time and the changes in radiation can be used as for example to maintain an active dispensing condition for the dispenser on a day when there are periods of strong radiation intermittently spaced at relatively short intervals by periods of lesser radiation as for example from clouds which significantly reduce the radiation. Similarly the dispenser may be controlled to be inactive on days when high radiation exists for a short periods of time interspaced by longer time periods of lower radiation.

Figure 4:
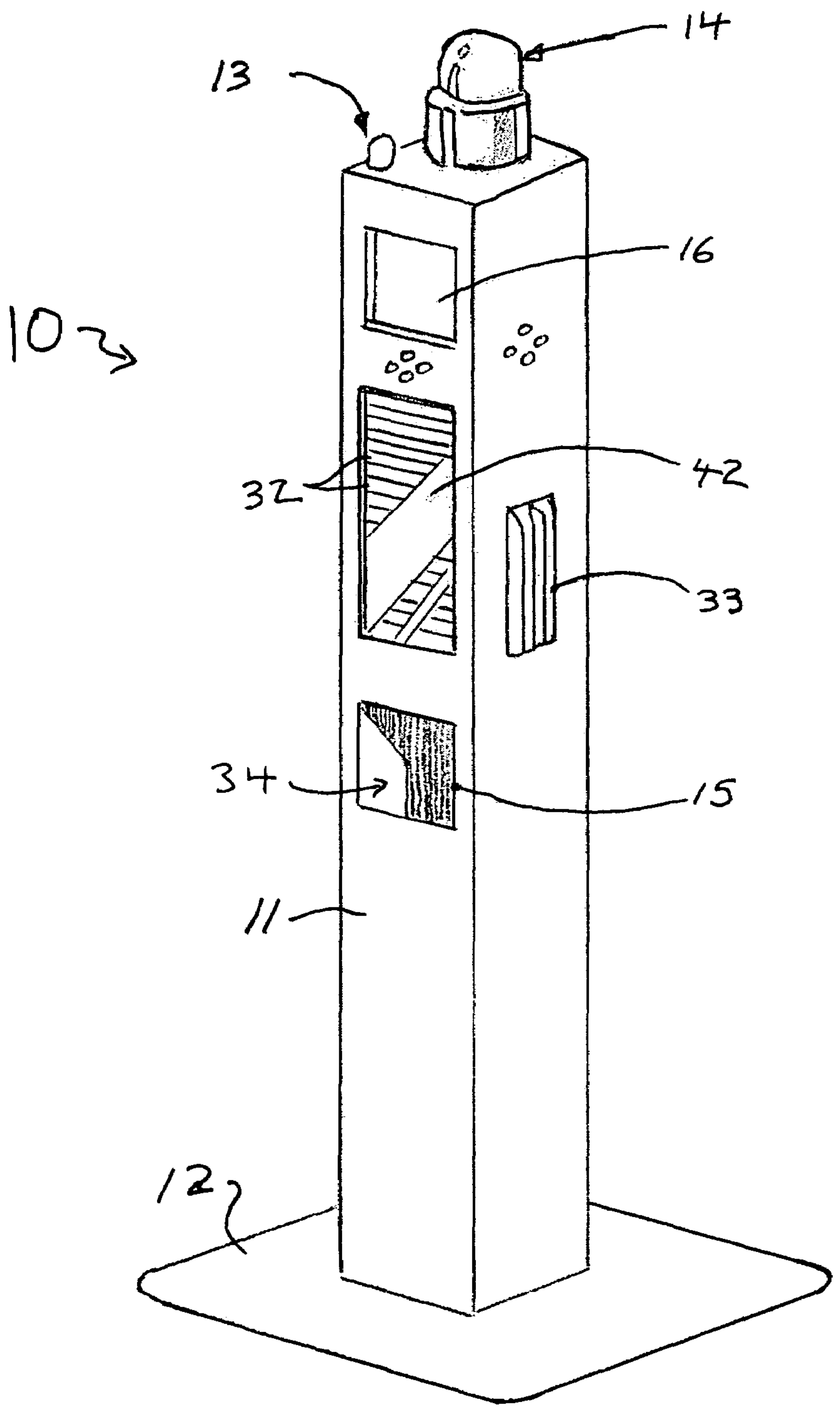
FIG. 4 is a pictorial view of a dispenser comprising an automated vending machine in accordance with a second embodiment of the invention.

Reference is made to FIG. 4 which illustrates a second embodiment of a dispensing tower 11 in accordance with the present invention. The dispensing tower 11 in the second embodiment differs from that shown in the first embodiment notably in that the dispensing mechanism is an automated vending machine which provides for an internal storage compartment for storage of individual packets 32 of product to be dispensed as for example individual packets of sunscreen. In FIG. 4, a window 42 is provided permitting a user to view the individual packets 32 to be dispensed. The dispenser 10 includes a mechanism for receiving payment in the form of a card reader 33 which may be swiped with a credit or debit card for extracting payment. While not shown, an alternate payment method may be provided as for example to receive coin or paper money.

On providing suitable payment as by the card reader 33, the dispensing mechanism 15 is activated to dispense an individual packet 32 which drops down from storage into a receiving bin 34 for retrieval by a user.

In accordance with the embodiment of the invention in FIG. 4, the dispenser 10 when intended to produce revenues, may be controlled so as to always be active and thus the dispensing mechanism 15 may be independent of the radiation sensor 13. The radiation sensor 13 is preferably used such that the control mechanism 40 will activate the warning/notification mechanisms as a manner of attracting purchasers. The control mechanism 40 may control operation of the warning/notification mechanisms to provide warning signals under whatever conditions are desired toward selling product, however preferably with increased warnings provided with increased radiation sensed. While the automated dispenser 10 as shown is intended for dispensing of individual packets of lotion, it is to be understood that on payment being received by a card reader and/or coin operated system, an automated dispenser of the type shown in FIG. 1 could then be activated for dispensing of a single allotment fluid.

Preferred use of the dispenser 10 of FIG. 1 can be in school settings as with children. The fingerprint reader 25 could be monitored as a method of ensuring that excessive sunscreen lotion is not dispensed to any one child and in addition as a method of determining what children have received sunscreen and what children have not received sunscreen. The dispenser of FIG. 1 could also be useful for use at other controlled outdoor events as soccer tournaments, baseball games, tennis, camps and the like where controlled dispensing of the sunscreen may be preferred possibly with monitoring of who uses and what uses are made.

Preferred use of the dispenser 10 of FIG. 4 might be at any outdoor location where it may be desired to sell products to persons. For sale of sunscreens, locations such as at sports events, including golf tournaments and tennis tournaments may be preferred. Both the dispensers of FIG. 1 and FIG. 4 may be portable and self-contained, as by being powered by batteries, possibly supplemented by solar panels to recharge the battery. Credit card authorization can be obtained for a card reader by a telephone to check for authorization, as by a cellular phone included as part of the tower control mechanism.

The first embodiment of FIG. 1 shows a fingerprint reader as one identification mechanism for identification of a user. Other identification mechanisms may comprise voiceprints or passwords or names to be keyed in by a user as on a keyboard (not shown) attached to the tower.

While the invention has been described with reference to preferred embodiment, many modifications and variations will now be apparent to persons skilled in the art. For a definition of the invention reference is made to the following claims.

I claim:

1. In combination:

(i) a radiation sensing mechanism, (ii) an alarm mechanism, and (iii) a dispensing mechanism, the radiation sensing mechanism sensing radiation and providing an output signal representative of radiation impinging on the sensing mechanism, the alarm mechanism to disseminate either an audible or a visual alarm perceptive to a person in proximity of the dispensing mechanism, the dispensing mechanism to dispense product on demand by a user, wherein when radiation impinging as the radiation sensing mechanism is above a predetermined level, the output signal activating the alarm mechanism to disseminate the alarm.

2. The combination as claimed in claim 1 wherein the dispensing mechanism has an inoperative mode and an operative mode, the dispensing mechanism is in the operative mode for dispensing of product on demand when the output signal is representative of radiation above the predetermined level and is in the inoperative mode to prevent dispensing product when the output signal is representative of radiation below the predetermined level.

3. The combination as claimed in claim 1 wherein the product is a sunscreen useful for applying to human skin to reduce the effects of ultra violet radiation.

4. The combination as claimed in claim 1 wherein the alarm mechanism is selected from one or more of the group comprising a lamp, a flashing lamp, a rotating lamp, a plurality of different coloured lamps, a mechanism generating audible sounds or spoken words and written warning message, and a control mechanism to receive the output signal and control operation of the alarm mechanism having regard to the output signals.

5. A combination as claimed in claim 1 wherein the radiation sensing mechanism senses levels of ultra violet radiation.

6. In combination:

(i) a radiation sensing mechanism, (ii) an alarm mechanism, and (iii) a dispensing mechanism, the radiation sensing mechanism sensing radiation and providing output signals representative of radiation impinging on the sensing mechanism, the alarm mechanism to disseminate either an audible or a visual alarm perceptive to a person in proximity of the dispensing mechanism, the dispensing mechanism to dispense product on demand by a user, and a control mechanism to receive the output signals and control operation of the alarm mechanism having regard to the output signals.

7. A combination as claimed in claim 5 wherein the control mechanism also controls operation of the dispensing mechanism.

8. A combination as claimed in claim 6 wherein the control mechanism controls the dispensing mechanism to prevent dispensing of product on demand by a user having regard to certain factors.

9. A combination as claimed in claim 6 including an identification mechanism for identification of a user.

10. A combination as claimed in claim 9 wherein the identification mechanism comprises a fingerprint reader.

11. A combination as claimed in claim 9 wherein the control mechanism maintains a database of identification data for identifying individual users, the control mechanism requires identification data input by a of a user to the identification mechanism to match identification data in the database as a prerequisite to activating the dispensing mechanism to dispense product on demand by any user.

12. A combination as claimed in claim 9 wherein the control mechanism maintains a database of identification data for identifying individual users who have demanded product be dispensed and prevents dispensing of an additional quantity of product to a user who inputs the same identification data for a period of time after initial dispensing.

13. A combination as claimed in claim 6 including a mechanism to receive payment from a user.

14. A combination as claimed in claim 13 wherein the dispensing mechanism dispensing product only on receipt of payment by the mechanism to receive payment.

15. A combination as claimed in claim 6 wherein the control mechanism controls the alarm mechanism such that as the radiation impinging on the radiation sensor increases the extent to which the alarm mechanism disseminate alarm is increased.

16. A combination as claimed in claim 7 wherein the control mechanism controls operation of the alarm mechanism controls operation of the alarm mechanism and dispensing mechanism having regard to one or more factors selected from the group consisting of the output signals from the radiation sensor, the change in the output signals with time, time of day, calendar date, latitude of the dispensing mechanism and longitude of the dispensing mechanism.

17. A combination as claimed in claim 6 wherein the control mechanism controls the dispensing mechanism to not dispense when the output signals are indicative of radiation levels below a predetermined minimum.

18. A combination as claimed in claim 17 wherein the control mechanism controls the dispensing mechanism to activate the alarm mechanism and to permit the dispensing mechanism to dispense on demand by a user when the output signals are indicative of radiation levels above a predetermined minimum.

19. A combination as claimed in claim 11 wherein the control mechanism keeps a record of users who have demanded that product be dispensed and can provide a list of users who have not demanded the product be dispensed.

* * * * *